(12) United States Patent
Yoshikiyo et al.

(10) Patent No.: US 7,396,950 B2
(45) Date of Patent: Jul. 8, 2008

(54) PROCESS FOR PRODUCTION OF TRIALKOXYHALOSILANES

(75) Inventors: Motozo Yoshikiyo, Chiba (JP); Yasuhiro Tanaka, Chiba (JP); Toshikazu Machida, Chiba (JP); Hiroshi Sato, Chiba (JP); Nobuyuki Kuroda, Yamaguchi (JP); Mitsumasa Tsugawa, Yamaguchi (JP); Sanae Hatakenaka, Yamaguchi (JP); Mikio Fujimoto, Yamaguchi (JP)

(73) Assignee: Ube Industries, Ltd. (JP)

( * ) Notice: Subject to any disclaimer, the term of this patent is extended or adjusted under 35 U.S.C. 154(b) by 0 days.

(21) Appl. No.: 11/751,308

(22) Filed: May 21, 2007

(65) Prior Publication Data

US 2007/0255068 A1    Nov. 1, 2007

Related U.S. Application Data

(62) Division of application No. 10/565,423, filed as application No. PCT/JP2004/012839 on Sep. 3, 2004, now abandoned.

(30) Foreign Application Priority Data

| Sep. 8, 2003 | (JP) | ............................... 2003-315705 |
| Dec. 16, 2003 | (JP) | ............................... 2003-417477 |
| Mar. 1, 2004 | (JP) | ............................... 2004-055610 |
| Mar. 1, 2004 | (JP) | ............................... 2004-055611 |
| Mar. 12, 2004 | (JP) | ............................... 2004-070498 |
| Aug. 23, 2004 | (JP) | ............................... 2004-242314 |

(51) Int. Cl.
*C07F 7/02*    (2006.01)

(52) U.S. Cl. ........................ 556/410; 556/482; 556/484

(58) Field of Classification Search .................. 556/410, 556/483, 484, 482

See application file for complete search history.

(56) References Cited

U.S. PATENT DOCUMENTS 4,491,669 A * 1/1985 Arkles et al. ................. 556/410

FOREIGN PATENT DOCUMENTS

| JP | 0 045 975 A2 | 2/1982 |
| JP | 57-63310 | 4/1982 |
| JP | 57-63311 | 4/1982 |
| JP | 58-083016 | 5/1983 |
| JP | 59-058010 | 4/1984 |
| JP | 60-044507 | 3/1985 |
| JP | 62-011705 | 1/1987 |
| JP | 63-223008 | 9/1988 |
| JP | 63-259807 | 10/1988 |
| JP | 02-084404 | 3/1990 |
| JP | 04-202505 | 7/1992 |
| JP | 04-370103 | 12/1992 |
| JP | 05-310751 | 11/1993 |
| JP | 08-003215 | 1/1996 |
| JP | 08-100019 | 4/1996 |
| JP | 08-120021 | 5/1996 |
| JP | 08-143620 | 6/1996 |
| JP | 08-143621 | 6/1996 |
| JP | 08-157519 | 6/1996 |
| JP | 08-231663 | 9/1996 |
| JP | 09-040714 | 2/1997 |
| JP | 2000-001493 | 1/2000 |

OTHER PUBLICATIONS

Peppard, Donald F. et al.; "Preparation and Synthetic Applications of Alkyl Chlorosilicates"; vol. 68; p. 70-72; Jan. 1946; USA.
Chernyshev, E.N. et al.; "Reaction of Tetraethoxysilane with Silicon Tetrachloride Synthesis of Triethoxychlorosilane"; Russian Journal of General Chemistry; vol. 65, No. 7, Part 2, 1995.
Kirichenko, E.A., et. al.; Abstract, "Infrared-spectroscopic study of some aminosilanes"; Trudy Instituta; No. 70; p. 140-2; 1972; Russia.
Yankov, L. et al.; Abstract, "Vapor-liquid method for the preparation of homogeneous and mixed tetraalkoxy- and different alkoxychlorosilanes"; Khimiya i Industriya; 1983; Bulgaria.
Zhurnal Obshchei Khimii, vol. 65, p. 1142 (1995).

* cited by examiner

*Primary Examiner*—Caixia Lu
(74) *Attorney, Agent, or Firm*—Trexler, Bushnell, Giangiorgi, Blackstone & Marr, Ltd.

(57) ABSTRACT

A process for the production of trialkoxyhalosilanes which comprises reacting a tetrahalosilane [37] with a tetra-alkoxysilane [38] in the presence of an alcohol whose alkoxy group is the same as those of the tetraalkoxysilane to thereby obtain a trialkoxyhalosilane [39], characterized in that the alcohol is used in an amount of 5 to 50% by mole based on the total amount of Si of the tetrahalosilane and the tetraalkoxysilane: $SiX_4$ [37] (wherein X is halogeno) $Si(OR^1)_4$ [38] (wherein $R^1$ is a hydrocarbon group having 1 to 6 carbon atoms) $XSi(OR^1)_3$ [39] (wherein X and $R^1$ are each as defined above).

4 Claims, 4 Drawing Sheets

US 7,396,950 B2

PROCESS FOR PRODUCTION OF TRIALKOXYHALOSILANES

PRIORITY

This application is a division of U.S. patent application Ser. No. 10/565,423, filed on May 22, 2006, which is a national-phase filing under Section 371 of PCT/JP04/12839 filed on Sep. 3, 2004, the disclosures of all of which are incorporated herein by reference.

FIELD OF THE INVENTION

The present invention relates to a novel process for production of trialkoxyhalosilanes, and a novel process for production of alkoxy(dialkylamino) silanes. It also relates to a catalyst for polymerization or copolymerization of α-olefins, a catalyst component therefor, and a process for polymerization of α-olefins ith the catalyst.

BACKGROUND OF THE INVENTION

An alkoxy(dialkylamino) silane can be produced in a known process, which comprises reacting an alkoxysilane with a Grignard reagent for introduction of an amino group, and in another known process of production, which uses an alkoxy halosilane as a raw material.

The processes for production of alkoxy halosilanes, which comprise reacting a tetrasilane with an alcohol, are disclosed in Non-Patent Document 1 (J. Am. Chem. Soc., Vol 68, p. 70, 1946) and Non-Patent Document 2 (Khimiya i Industriya, No. 6, p. 248, 1983).

Non-Patent Document 1 shows an experimental example using a tetrachlorosilane and an allyl alcohol under an experimental condition to obtain a triallyloxychlorosilane as a major product in which the tetrachlorosilane is reacted with the allyl alcohol at a molar ratio of 1:2.5. The yield is 53% and a much higher yield is required, needless to say. As for other kinds of alkoxychlorosilanes, such as chloro trimethoxysilane, chlorotriethoxysilane, dichlorodiethoxy silane and trichloroethoxysilane, though they can be assumably synthesized because boiling points and physical property values are described, there is no description about yields.

In Non-Patent Document 2, details such as experimental conditions are unavailable. The study abstract described in the chemical abstract No. 100:34098 shows that, among chloro ethoxysilanes as alkoxyhalosilanes, a trichloroethoxysilane with introduction of one ethoxy group is obtained at a yield of 90%, and a dichloroethoxysilane with introduction of two ethoxy groups is obtained at a yield of 95%, but a chloroethoxysilane with introduction of three ethoxy groups is obtained at a lower yield of 80%. Further, the reaction condition described includes reaction temperatures of 100-145° C., and much lower temperatures are desired.

On the other hand, Patent Document 1 (JP-A 5-310751) proposes a process for production of alkoxyhalosilanes through reaction of a tetrachlorosilane with a tetraalkoxysilane. It shows the use of an acid as a catalyst. An acid with a higher boiling point, however, causes reduction in yield in accordance with separation failures or heating under coexistence during distillation, isolation and purification of a product. Titanium tetrachloride, aluminum chloride and boron fluoride shown as examples of Lewis acid are sensitive to humidity in the atmosphere and generally have difficulties in handing. On the other hand, hydrogen halides are gases at room temperature under normal pressure and easily removable from reaction systems. This Document shows direct introduction into the reaction system and examples of generation in the system by $H_2O$. In general, however, the need for giving attention to handing gaseous hydrogen halides increases the cost of the facility. Though the generation in the system by $H_2O$ can be considered safe and less costly, a silane halide is consumed by the extent of introduction of $H_2O$ and converted into a compound having a Si—D bond different from the aimed alkoxysilane halide. Accordingly, a problem arises because a Si-based yield is lowered. The more the quantity of the catalyst, the more the reduction in production cost can be desired because of the effect of shortening the reaction time. In this case, however, the above method requires a large amount of $H_2O$ to be introduced, which inevitably invites reduction in yield as a drawback. Examples of Patent Document 1 have yields of 60-75% at most and there is a need for processes capable of achieving much higher yields.

With respect to chlorotriethoxysilanes, Non-Patent Document 3 (Zhurnal Obshchei Khimii, vol. 65, p. 1142, 1995) discloses that when a tetrachlorosilane is reacted with a tetraalkoxysilane under condition of heating at 40° C. in the presence of 0.02-1.0 wt. % ethanol, $ClSi(OEt)_3$ can be obtained at a maximum yield of 90% based on Cl in the raw material composition. Similar to the yields exemplified in the preceding paragraphs, however, the yield based on Si important on cost computation in the raw material composition is 82%. Accordingly, much higher yields are still required. Implementation without humidification is also desired.

Non-Patent Document 4 (Trudy Instituta-Moskovskii Khimiko-Tekhnokogcheskii Institut imeni D.I. Mendeleeva (1972), No. 70 140-2) reports that reaction of $ClSi(OEt)_3$ with $Et_2NH$ yields $Et_2NSi(OEt)_3$. Isolation/purification of $ClSi(OEt)_3$ is not preferable, however, because it causes substance loss not a little and increases purification steps.

On the other hand, in recent years, for polymerization of α-olefins, JP-A 57-63310 (Patent Document 2), JP-A 57-63311 (Patent Document 3), JP-A 58-83016 (Patent Document 4), JP-A 59-58010 (Patent Document 5) and JP-A 60-44507 (Patent Document 6) propose many a high-activity carrier catalyst system. The system comprises a solid catalyst component essentially including magnesium, titanium, a halogen element and an electron donor; an organometallic compound of a I-III group metal in the periodic table; and an electron donor. Further, JP-A 62-11705 (Patent Document 7), JP-A 63-223008 (Patent Document 8), JP-A 63-259807 (Patent Document 9), JP-A 2-84404 (Patent Document 10), JP-A 4-202505 (Patent Document 11) and JP-A 4-370103 (Patent Document 12) disclose polymerization catalysts characterized by the use of a specific organosilicon compound as the electron donor. For example, JP-A 2-84404 (Patent Document 13) discloses a process in which a cyclopentylalkyldimethoxysilane or a dicyclopentyl dimethoxysilane is employed as the electron donor. The catalyst system using such the silicon compound is not always excellent in hydrogen response. JP-A 63-223008 (Patent Document 14) discloses a catalyst system using a di n-propyldimethoxy silane excellent in hydrogen response as the electron donor. The system can not satisfy stereomainity, however, and has a problem because the stiffness of an α-olefin polymer can not be enhanced.

JP-A 9-40714 (Patent Document 15) discloses an alkoxysilane compound having an aliphatic amino substituent. JP-A 8-3215 (Patent Document 16), JP-A 8-100019 (Patent Document 17) and JP-A 8-157519 (Patent Document 18) propose processes for production of α-olefins using an alkoxysilane having an aliphatic amino substituent as the catalyst component. These processes, however, can not always satisfy hydrogen response in performance particularly. JP-A 8-143620 (Patent Document 19) proposes a process for production of α-olefins using a dialkoxysilane having two aliphatic amino substituents as the electron donor. The process, however, can not always satisfy polymerization activity and stereomainity in performance.

JP-A 8-120021 (Patent Document 20), JP-A 8-143621 (Patent Document 21) and JP-A 8-231663 (Patent Document 22) disclose processes using cycloaminosilane compounds. The use of these specifically described compounds as the catalyst component can achieve high stereomainity but can not always satisfy hydrogen response.

The carrier catalyst system using the electron donor can not always satisfy the balance among polymerization activity, stereomainity and hydrogen response in performance. Accordingly, a further improvement is desired.

In recent years, in the field of injection molding mainly aimed at automobile materials and household electrical appliance materials, for the purpose of thinning and light-weighting of goods, there are increased needs for α-olefin polymers with high melt fluidity, high stiffness and high heat resistance. For production of such the α-olefin polymers, the use of a catalyst with high hydrogen response is important on polymerization. Specifically, for adjustment of the molecular weight of an α-olefin polymer, hydrogen is generally employed as a chain transfer agent that coexists in the polymerization system. In particular, elevation of the melt fluidity of the α-olefin polymer requires the molecular weight lowered by hydrogen. A melt flow rate is employed as an index for the melt fluidity of the α-olefin polymer. The lower the molecular weight of the α-olefin polymer, the higher the melt flow rate becomes relationally. Lower hydrogen response requires a large quantity of hydrogen in the polymerization system to elevate the melt flow rate of the α-olefin polymer. To obtain the α-olefin polymer with the same flow rate, higher hydrogen response does not require the quantity of hydrogen as large as the lower hydrogen response requires. Therefore, the lower hydrogen response requires introduction of an excessive quantity of hydrogen into the polymerization system to elevate the melt flow rate of the α-olefin polymer. Accordingly, in production processes, for safety, a polymerization device with a limited resistance to pressure elevates partial pressure of hydrogen. In such the relation, the polymerization temperature should be lowered, exerting an ill effect on the production speed and the quality as a problem.

The above-described organosilicon compounds are synthesized using an organometallic reagent such as a Grignard reagent and accordingly the raw material reagent is expensive. Therefore, the use of the organosilicon compound synthesized in the process to produce an α-olefin polymer inevitably makes the α-olefin polymer itself expensive and causes a problem on production cost.

Patent Document 1: JP-A 5-310751

Patent Document 2: JP-A 57-63310

Patent Document 3: JP-A 57-63311

Patent Document 4: JP-A 58-83016

Patent Document 5: JP-A 59-58010

Patent Document 6: JP-A 60-44507

Patent Document 7: JP-A 62-11705

Patent Document 8: JP-A 63-223008

Patent Document 9: JP-A 63-259807

Patent Document 10: JP-A 2-84404

Patent Document 11: JP-A 4-202505

Patent Document 12: JP-A 4-370103

Patent Document 13: JP-A 2-84404

Patent Document 14: JP-A 63-223008

Patent Document 15: JP-A 9-40714

Patent Document 16: JP-A 8-3215

Patent Document 17: JP-A 8-100019

Patent Document 18: JP-A 8-157519

Patent Document 19: JP-A 8-143620

Patent Document 20: JP-A 8-120021

Patent Document 21: JP-A 8-143621

Patent Document 22: JP-A 8-231663

Non-Patent Document 1: J. Am. Chem. Soc., Vol 68, p. 70, 1946

Non-Patent Document 2: Khimiya i Industriya, No. 6, p. 248, 1983

Non-Patent Document 3: (Zhurnal Obshchei Khimii, vol. 65, p. 1142, 1995)

Non-Patent Document 4: Trudy Instituta-Moskovskii Khimiko-Tekhnokogcheskii Institut imeni D. I. Mendeleeva (1972), No. 70 140-2

SUMMARY OF THE INVENTION

Problems to be Solved in the Invention

The present invention solves the problems in the above-described conventional processes for production of alkoxyhalosilanes and has a first object to provide a novel process for production of trialkoxyhalosilanes.

The present invention solves the problems in the above-described conventional processes for production of alkoxy (dialkylamino)silanes and has a second object to provide a novel process for production of trialkoxy(dialkylamino)silanes.

The present invention solves the problems in the above-described conventional polymerization of α-olefins and has a third object to provide α-olefin polymers or copolymers with higher hydrogen response, higher polymerization activity, higher stereomainity, better melt fluidity and lower production costs.

Means for Solving the Problems

To achieve the first object, the present invention provides a first process for production of trialkoxyhalosilanes, which comprises reacting a tetrahalosilane represented by Formula 19 with a tetraalkoxysilane represented by Formula 20 in the mixture of an alcohol composed of the same alkoxy group as that of the tetraalkoxysilane to yield a trialkoxyhalosilane represented by Formula 21, wherein the alcohol is used in an amount of 5-50% by mol based on a total amount of Si in the tetrahalosilane and the tetraalkoxysilane.

$$SiX_4 \qquad \text{[Formula 19]}$$

(Where X Denotes Halogen)

$$Si(OR^1)_4 \qquad \text{[Formula 20]}$$

(where R¹ denotes a hydrocarbon group having 1-6 carbon atoms)

$$XSi(OR^1)_3 \quad \text{[Formula 21]}$$

(where X denotes halogen; and R¹ a hydrocarbon group having 1-6 carbon atoms).

To achieve the first object, the present invention provides a second process for production of trialkoxyhalosilanes, which comprises reacting a tetrahalosilane represented by Formula 22 with an alcohol represented by Formula 23 at a controlled temperature of 40° C. or below to yield a trialkoxyhalosilane represented by Formula 24.

$$SiX_4 \quad \text{[Formula 22]}$$

(Where X Denotes Halogen)

$$R^1OH \quad \text{[Formula 23]}$$

(where R¹ denotes a hydrocarbon group having 1-6 carbon atoms)

$$XSi(OR^1)_3 \quad \text{[Formula 24]}$$

(where X denotes halogen; and R¹ a hydrocarbon group having 1-6 carbon atoms).

To achieve the second object, the present invention provides a process for production of trialkoxy(dialkylamino)silanes, which comprises a first step including the first or second process for production of trialkoxyhalosilanes; and a second step of reacting the trialkoxyhalosilane obtained in the first step with a dialkylamine represented by Formula 25 to yield a trialkoxy(dialkylamino)silane represented by Formula 26.

$$R^2R^3NH \quad \text{[Formula 25]}$$

(where R² denotes a hydrocarbon group having 1-12 carbon atoms; and R³ a hydrocarbon group having 1-12 carbon atoms)

$$R^2R^3NSi(OR^1)_3 \quad \text{[Formula 26]}$$

(where R¹ denotes a hydrocarbon group having 1-6 carbon atoms; R² a hydrocarbon group having 1-12 carbon atoms; and R³ a hydrocarbon group having 1-12 carbon atoms).

To achieve the third object, the present invention provides a first catalyst component for polymerization or copolymerization catalysts of α-olefins, which comprises a mixture of silane compounds represented by Formulae 27 and 28.

$$Si(OR^1)_3R^2 \quad \text{[Formula 27]}$$

(where R¹ denotes a hydrocarbon group having 1-6 carbon atoms; and R² a hydrocarbon group having 1-12 carbon atoms, an amino group including a hydrogen atom and a hydrocarbon group having 1-12 carbon atoms, which are bonded on a N atom, or an amino group including two hydrocarbon groups each having 1-12 carbon atoms, which are bonded on a N atom (the two hydrocarbon groups may be the same or different from each other))

$$SiR^3_4 \quad \text{[Formula 28]}$$

(where R³ denotes an alkoxy group having 1-6 carbon atoms, a hydrocarbon group having 1-12 carbon atoms, an amino group including a hydrogen atom and a hydrocarbon group having 1-12 carbon atoms, which are bonded on a N atom, or an amino group including two hydrocarbon groups each having 1-12 carbon atoms, which are bonded on a N atom (the two hydrocarbon groups may be the same or different from each other). Each R³ may be the same as or different from another. Formulae 27 and 28 do not represent the same compound).

To achieve the third object, the present invention provides a second catalyst component for polymerization or copolymerization catalysts of α-olefins, which comprises a mixture of silane compounds represented by Formulae 29 and 30.

$$Si(OR^1)_3(NR^4R^5) \quad \text{[Formula 29]}$$

(where R¹ denotes a hydrocarbon group having 1-6 carbon atoms; R⁴ a hydrocarbon group having 1-12 carbon atoms, or a hydrogen atom; and R⁵ a hydrocarbon group having 1-12 carbon atoms)

$$Si(R^6)_n(NR^7R^8)_{4-n} \quad \text{[Formula 30]}$$

(where R⁶ denotes a hydrocarbon group having 1-12 carbon atoms or an alkoxy group having 1-6 carbon atoms (each R⁶ may be the same as or different from another); R⁷ a hydrocarbon group having 1-12 carbon atoms; R⁸ a hydrocarbon group having 1-12 carbon atoms; and n is equal to 1-2 or 4).

To achieve the third object, the present invention provides a third catalyst component for polymerization or copolymerization catalysts of α-olefins, which comprises a reacted mixture of a trialkoxyhalosilane represented by Formula 35 with a dialkylamine represented by Formula 36.

$$XSi(OR^1)_3 \quad \text{[Formula 35]}$$

(where X denotes halogen; and R¹ denotes a hydrocarbon group having 1-4 carbon atoms)

$$R^2R^3NH \quad \text{[Formula 36]}$$

(where R² denotes a hydrocarbon group having 1-12 carbon atoms; and R³ a hydrocarbon group having 1-12 carbon atoms).

Effects of the Invention

The process for production of trialkoxyhalosilanes according to the present invention is possible to provide trialkoxyhalosilanes at higher yields.

The process for production of trialkoxy(dialkylamino)silanes according to the present invention is possible to provide trialkoxy(dialkylamino)silanes at higher yields.

The catalyst component according to the present invention can be employed to inexpensively produce α-olefin polymers with higher hydrogen response, higher polymerization activity, higher stereomainity and better melt fluidity. Particularly, the greatly improved hydrogen response over the conventional catalyst systems allows α-olefin polymers with high stiffness and nice melt fluidity to be produced at no sacrifice of productivity. The use of the catalyst system of the present invention allows production of an ethylene-propylene copolymer at a block rate of 10-50 wt. % and production of a reactor-made TPO. The organosilicon compound of the catalyst component of the present invention does not contain the conventional expensive organometallic compound and the distillation/purification process on synthesis of the catalyst component can be simplified. Therefore, it is possible to synthesize an organosilicon compound at a lower production cost. In a word, the use of the catalyst component of the present invention allows production of α-olefin polymers inexpensively.

DETAILED DESCRIPTION OF THE INVENTION

First Process for Production of Trialkoxyhalosilanes

Figure 1:
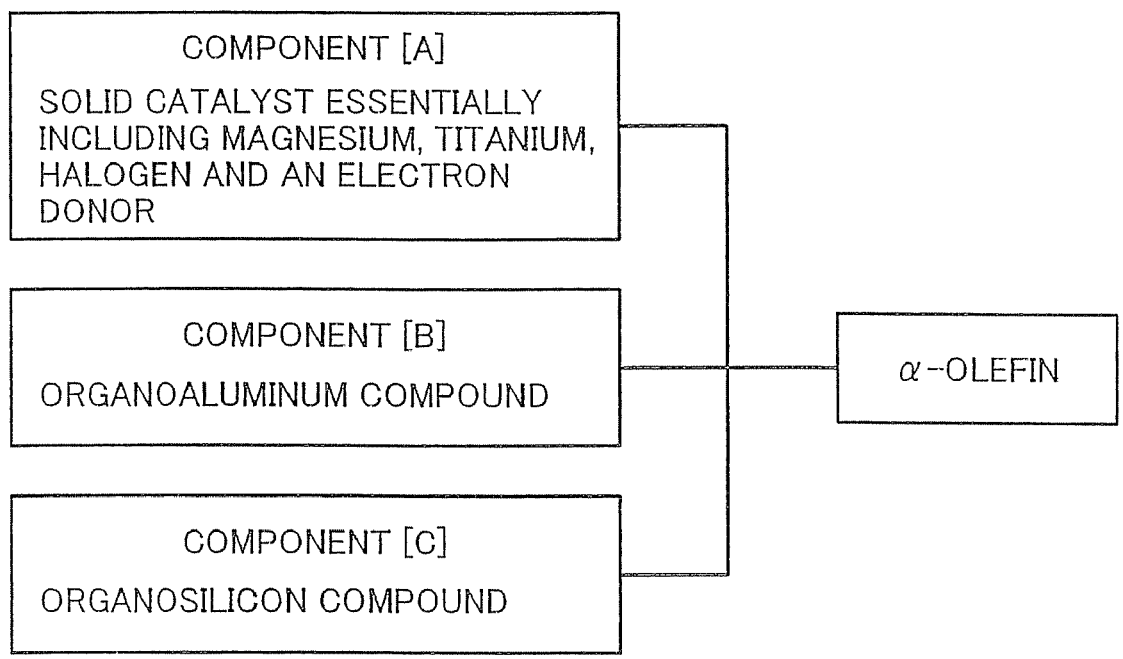
[FIG. 1] is a flowchart showing a preparation process and polymerization method of a catalyst component of the present invention.
Figure 2:
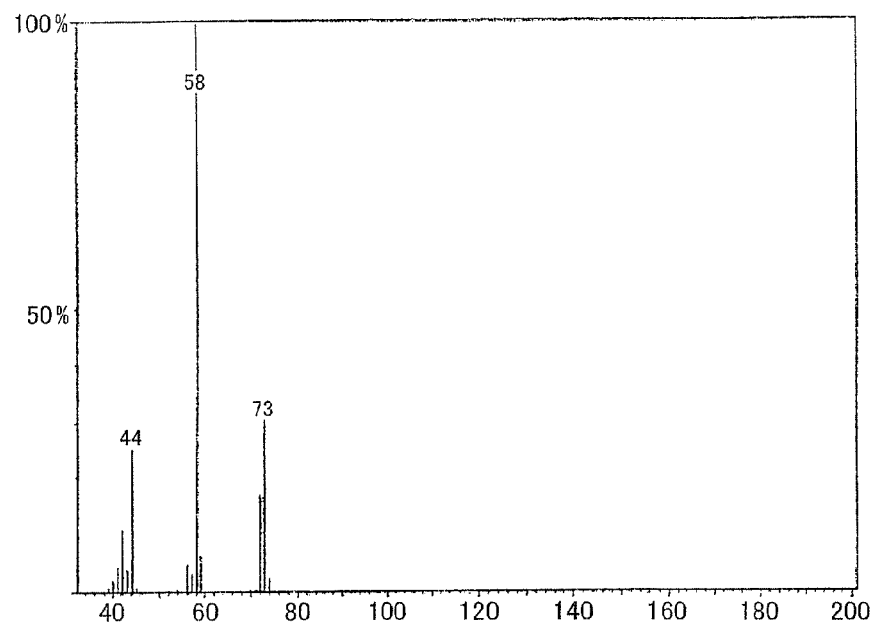
[FIG. 2] shows a mass spectrum of a diethylamine.
Figure 3:
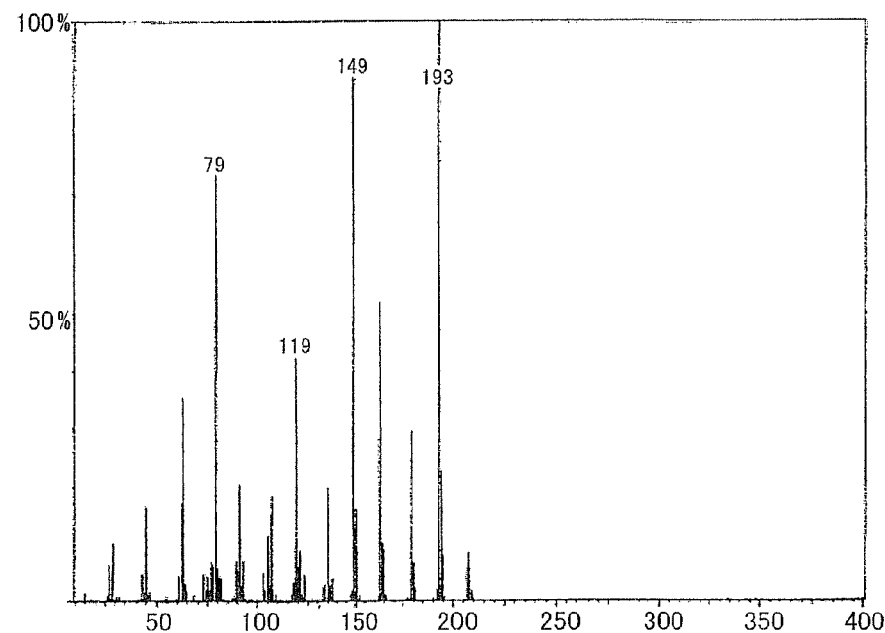
[FIG. 3] shows a mass spectrum of a tetraethoxysilane.
Figure 4:
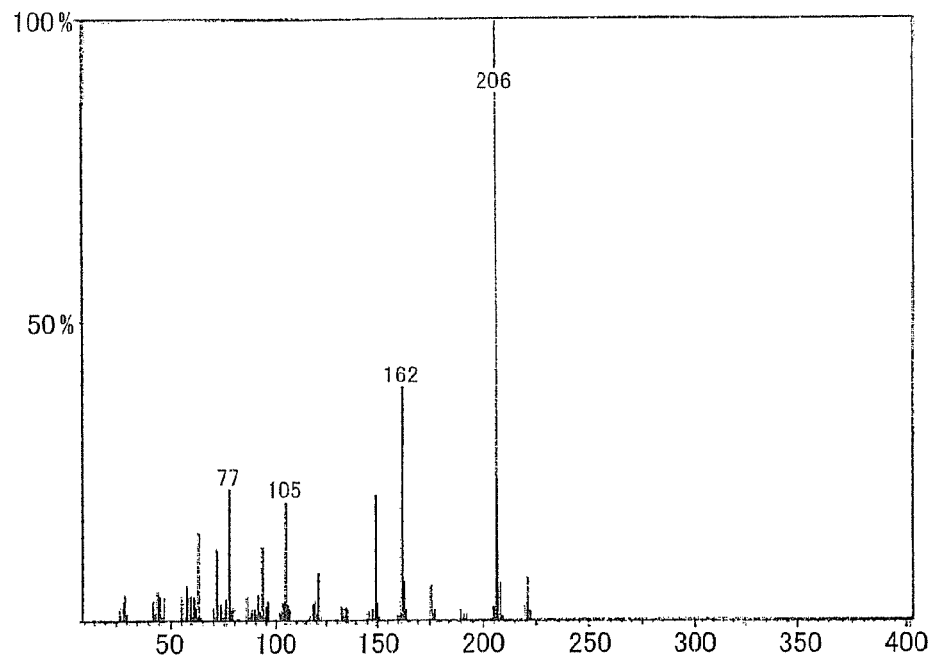
[FIG. 4] shows a mass spectrum of a diethylaminodiethoxy methoxysilane.
Figure 5:
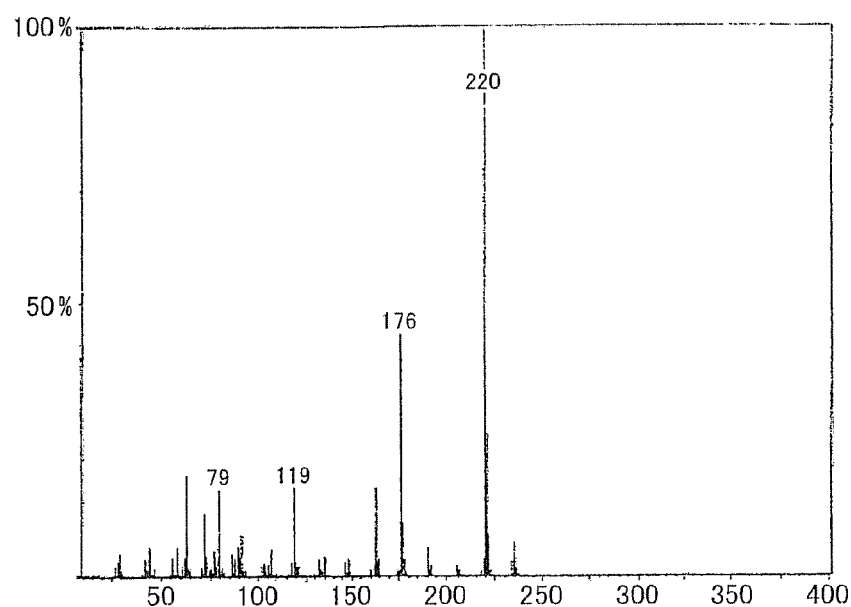
[FIG. 5] shows amass spectrum of a diethylaminotriethoxy silane.
Figure 6:
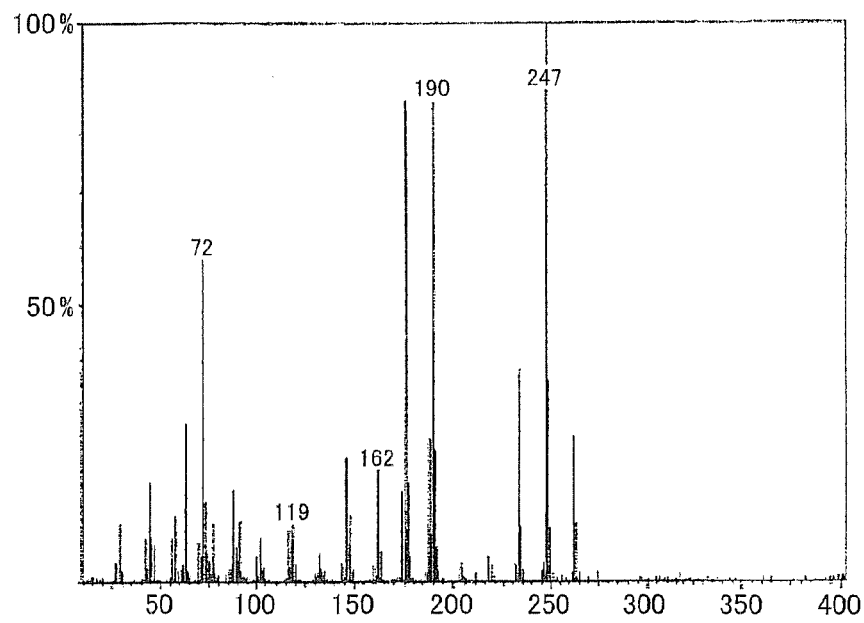
[FIG. 6] shows a mass spectrum of a bis(diethylamino) diethoxy silane.
Figure 7:
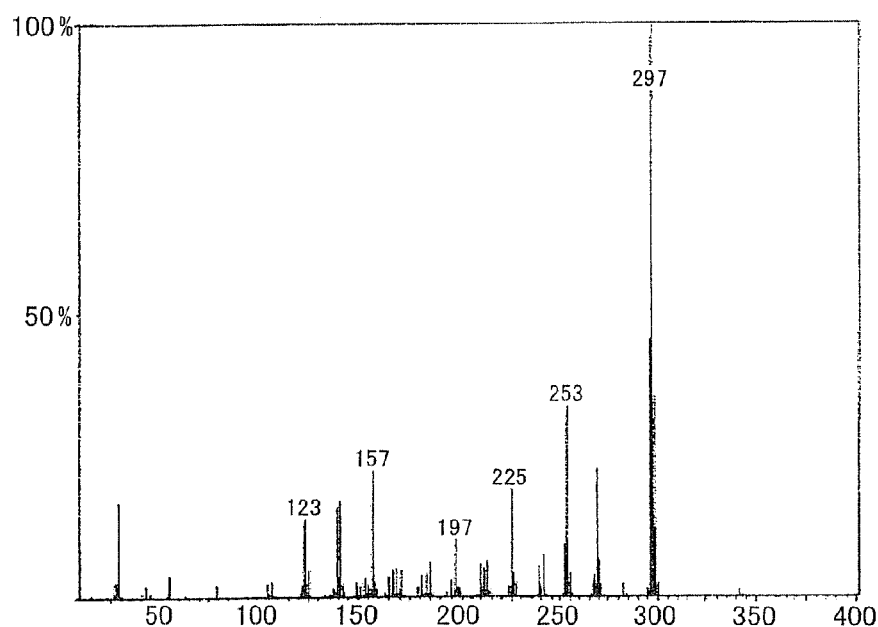
[FIG. 7] shows a mass spectrum of a hexaethoxydisiloxane.

A first process for production of trialkoxyhalosilanes employs the tetrahalosilane represented by Formula 19, such as tetrafluorosilane, tetrachlorosilane and tetrabromosilane. The tetrachlorosilane is preferable among those.

In the tetraalkoxyhalosilane represented by Formula 20, R1 is a hydrocarbon group having 1-6, preferably 2-6, more preferably 2-4 carbon atoms. The tetraalkoxyhalosilane represented by Formula 20 includes tetramethoxysilane, tetraethoxysilane, tetra-n-propoxysilane, tetra-iso-propoxy silane, tetra-n-butoxysilane and tetra-tert-butoxysilane. The tetraethoxysilane is preferable among those.

Though the first process for production of trialkoxyhalosilanes can proceed with no solvent, it may be performed with the use of a solvent that can not react with the raw material and the reacted product. When a solvent is employed, the solvent may include n-hexane, n-heptane, toluene, and diethyl ether.

The alcohol for use in the reaction system in the first process for production of trialkoxyhalosilanes reacts with a tetrahalosilane in the reaction system including the tetrahalosilane represented by Formula 19 and the tetraalkoxysilane represented by Formula 20 to generate a hydrogen halide in accordance with Expression 1.

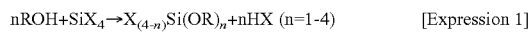

nROH+SiX$_4$→X$_{(4-n)}$Si(OR)$_n$+nHX (n=1-4)  [Expression 1]

In the reaction system including the tetrahalosilane represented by Formula 19, the tetraalkoxysilane represented by Formula 20 and an alcohol, an initial mixture can be expressed, based on a reaction equation obtained by substitution of n=4 into Expression 1, formally as a mixture of: a tetrahalosilane decreased by the extent equal to 0.25 times the molar quantity of the used alcohol; a tetraalkoxysilane increased by the extent equal to 0.25 times the molar quantity; and a hydrogen halide equal to an equivalent molar quantity of the alcohol. This reacted mixture can be converted into an equilibrated mixture of X$_{(4-m)}$Si(OR)$_m$ (where m=0-4). The generated hydrogen halide has an excellent catalytic action on interconversion of X$_{(4-m)}$Si(OR)$_m$ (where m=0-4). The use of the action achieves an effect on shortening the reaction time. Therefore, it is extremely desirable to keep the hydrogen halide in the reaction system. In a word, the first process for production of trialkoxyhalosilanes according to the present invention is preferably performed in the presence of an acid catalyst. Preferably, the acid catalyst is the hydrogen halide secondarily produced in the reaction.

A molar ratio of the tetrahalosilane represented by Formula 19 to the tetraalkoxysilane represented by Formula 20 is preferably 1:2.6 to 1:3.8 after the formal chemical conversion shown in the preceding paragraph. It is more preferably 1:3.0 to 1:3.4, and particularly preferably more than 1:3, in which a molar quantity of the tetraalkoxysilane in use is more than three times the molar quantity of the tetrahalosilane in use.

The amount of the alcohol for use in reaction is preferably 5-50% by mol, more preferably 10-30& by mol based on a total amount of Si in the tetrahalosilane represented by Formula 19 and the tetraalkoxysilane represented by Formula 20. A smaller amount in use than this range slows the reaction and a larger amount in use than this range lowers the yield.

In the first process of production of trialkoxyhalo silanes, a reaction temperature is preferably between −20 and 80° C., more preferably between 0 and 50° C. A lower temperature than this range slows the reaction and a higher temperature than this range lowers the solubility of the generated hydrogen halide undesirably. Preferably, the reaction time is 0.05-6.0 hrs.

Second Process for Production of Trialkoxyhalosilanes

A second process for production of trialkoxyhalosilanes employs the tetrahalosilane represented by Formula 22, such as tetrafluorosilane, tetrachlorosilane and tetrabromosilane. The tetrachlorosilane is preferable among those.

In the alcohol represented by Formula 23, R$^1$ is a hydrocarbon group having 1-6, preferably 2-6, and more preferably 2-4-carbon atoms. The alcohol represented by Formula 23 includes methanol, ethanol, 1-propanol, 2-propanol, and 1-butanol. The ethanol is preferable among those.

Though the reaction of the tetrahalosilane represented by Formula 22 with the alcohol represented by Formula 23 can proceed with no solvent it may proceed with the use of a solvent that can not react with the raw material and the reacted product. If a solvent is employed, the solvent may include n-hexane, n-heptane, toluene, and diethylether.

The reaction of the tetrahalosilane represented by Formula 22 with the alcohol represented by Formula 23 is an exothermic reaction that generates the hydrogen halide in accordance with the above Expression 1. This reaction converts the raw material of the tetrahalosilane represented by Formula 22 into an equilibrated mixture of X$_{(4-m)}$Si(OR)$_m$ (where m=0-4). The generated hydrogen halide has an excellent catalytic action on interconversion of X$_{(4-m)}$Si(OR)$_m$ (where m=0-4). The use of the action achieves an effect on shortening the reaction time. Therefore, it is extremely desirable to keep the hydrogen halide in the reaction system. In a word, the second process for production of trialkoxyhalosilanes according to the present invention is preferably performed in the presence of an acid catalyst. Preferably, the acid catalyst is the hydrogen halide secondarily produced in the reaction.

On the other hand, the solution of the hydrogen halide into the reacted product is an endothermic reaction. Through various studies on mixing methods and reaction containers, an unconventional condition has been found on controlling heat absorbing/radiating in accordance with the reaction using no special cooling machine to proceed the reaction at a low temperature in a short time. Namely, the hydrogen halide of the present invention has a reaction accelerating effect and a self-cooling effect.

A reaction temperature is preferably −50 to 40° C., and most preferably −20 to 30° C. from the viewpoint of no need for a special cooling facility. In a word, in the second process for production of trialkoxyhalosilanes, the reaction temperature is preferably controllable with no special cooling facility. Cooling down to −20° C. can be achieved by self-cooling or without cooling from external if heat absorbing in accordance with the solution of the hydrogen halide is utilized effectively. This is very preferable with respect to cost. The effective utilization of heat absorbing in accordance with the solution naturally increases the solved quantity of the hydrogen halide and exerts the reaction time shortening effect due to the catalytic action. On the other hand, at 40° C. or higher, dehydrohalogenation from the reacted solution becomes remarkable to eliminate the reaction time shortening effect. Though suppression of dehydrohalogenation can be solved if the reaction container has a pressure-proof hermetic structure, it requires a corresponding extra cost and results in a safety cost undesirably.

A reaction time is usually 0.25-72 hrs and controllable depending on the types and amounts of the tetrahalosilane and the alcohol as well as the reaction temperatures, preferably 0.25-3 hrs. Depending on the cases, it is preferable to execute a reaction at −20 to 5° C. for 0.25-24 hrs and then a reaction at 10 to 30° C. for 0.25-72 hrs.

A molar ratio of the tetrahalosilane represented by Formula 22 to the alcohol represented by Formula 23 is preferably 1:2.6 to 1:3.3, and more preferably 1:2.8 to 1:3.1.

Process for Production of Trialkoxy(dialkylamino)silanes

In the process for production of trialkoxy(dialkylamino) silanes according to the present invention, the reacted mixture obtained in the first step is preferably reacted with the dialkylamine represented by Formula 25 without isolation and purification.

In the process for production of trialkoxy(dialkylamino) silanes according to the present invention, the dialkylamine represented by Formula 25 may include dimethylamine, diethyl amine, dibutylamine and methylethylamine. The diethylamine is preferable among those.

In the dialkylamine represented by Formula 25, $R^2$ and $R^3$ denote a hydrocarbon group having 1-12, preferably 1-4 carbon atoms. In the second step of the process for production of trialkoxy(dialkylamino)silanes according to the present invention, if the dialkylamine represented by Formula 25 is inexpensive, a method with the use of a greatly excessive amount of the dialkylamine represented by Formula 25 is simple and preferable, also serving capture of the hydrogen halide produced in the reaction. When an excessive amount of the dialkylamine represented by Formula 25 is not employed, for the purpose of capture of the hydrogen halide produced in the reaction, a tertiary amine, such as triethylamine and N-ethyl-diisopropylamine, or a pyridine may be mixed. A reaction temperature is preferably −20 to 200° C., more preferably 0 to 120° C., and most preferably 10 to 80° C. from the viewpoint of no need for a heating or cooling facility. If the reaction temperature exceeds the boiling point, an inert gas such as nitrogen and argon may be employed to pressurize. A reaction time may be 0.25-120 hrs, preferably 0.25-3 hrs.

First or Second Catalyst Component for Polymerization or Copolymerization Catalysts of α-olefins In the first catalyst component for polymerization or copolymerization catalysts of α-olefins according to the present invention, $R^1$ in Formula 27 denotes a hydrocarbon group having 1-6, preferably 2-6 carbon atoms, which may include an unsaturated or saturated aliphatic hydrocarbon group having 1-6 carbon atoms. Specific examples may include methyl group, ethyl group, n-propyl group, isopropyl group, n-butyl group, isobutyl group, t-butyl group, and s-butyl group. The ethyl group is particularly preferable.

In Formula 27, $R^2$ is a hydrocarbon group having 1-12 carbon atoms, an amino group including a hydrogen atom and a hydrocarbon group having 1-12 carbon atoms, which are bonded on a N atom, or an amino group including two hydrocarbon groups each having 1-12 carbon atoms, which are bonded on a N atom (the two hydrocarbon groups may be the same or different from each other). Specific examples may include methyl group, ethyl group, propyl group, methylamino group, dimethylamino group, methylethylamino group, diethylamino group, ethyl n-propyl amino group, ethylisopropylamino group, methyl n-propylamino group, methylisopropylamino group, 1,2,3,4-tetrahydro quinolyl group, 1,2,3,4-tetrahydroisoquinolyl group, perhydro quinolyl group, and perhydroisoquinolyl group. The diethyl amino group is particularly preferable.

In the first or second catalyst component for polymerization or copolymerization catalysts of α-olefins according to the present invention, the organosilicon compound component represented by Formula 27 or 33 may include dimethylaminotriethoxysilane, diethylaminotriethoxysilane, diethylaminotrimethoxysilane, diethylaminotri n-propoxy silane, di n-propylaminotriethoxysilane, methyl n-propylamino triethoxysilane, t-butylaminotriethoxysilane, ethyl n-propylaminotriethoxysilane, ethylisopropylaminotriethoxy silane, and methylethylaminotriethoxysilane. Preferably, it may include diethylaminotriethoxysilane and diethylamino trimethoxysilane. These oroganosilicon compounds may be employed solely or in combination of two or more.

The organosilicon compound component represented by Formula 28 or 34 may include bisaminosilanes such as bis (dimethylamino)diethoxysilane, bis(diethylamino)diethoxy silane, bis(diethylamino)dimethoxysilane, bis(diethylamino) di n-propoxysilane, bis(di n-propylamino)diethoxysilane, bis (methyl n-propylamino)diethoxysilane, bis(t-butylamino)diethoxysilane, bis(ethyl n-propylamino)diethoxysilane, bis (ethylisopropylamino)diethoxysilane, and bis(methylethyl amino)diethoxysilane. It may also include tetraalkoxysilanes such as tetramethoxysilane, tetraethoxysilane, tetra n-propoxysilane, tetraisopropoxysilane, tetran-butoxysilane, tetraisobutoxysilane, tetra s-butoxysilane, and tetra t-butoxysilane. It may further include ethyltrimethoxysilane, methyldiethoxysilane, ethyldimethoxysilane, methyltriethoxy silane, dimethoxydiethoxysilane, ethyldiethoxysilane, tri ethoxymethoxysilane, ethyltriethoxysilane, and diethylamino diethoxysilane. These organosilicon compounds may be employed solely or in combination of two or more.

In the first or second catalyst component for polymerization or copolymerization catalysts of α-olefins according to the present invention, the silane compound represented by Formulae 27-34 may be synthesized by reacting a tetrahalosilane represented by Formula 31 with a tetraalkoxysilane represented by Formula 32 to yield a trialkoxyhalosilane represented by Formula 33, which is then reacted with a dialkylamine represented by Formula 34. In this synthesis, the reaction of the tetrahalosilane represented by Formula 31 with the tetraalkoxysilane represented by Formula 32 is performed preferably in the presence of an acid catalyst.

$$SiX_4 \qquad \text{[Formula 31]}$$

(where X denotes halogen)

$$Si(OR^1)_4 \qquad \text{[Formula 32]}$$

(where $R^1$ denotes a hydrocarbon group having 1-6, preferably 2-6 carbon atoms)

$$XSi(OR^1)_3 \qquad \text{[Formula 33]}$$

(where X denotes halogen; and $R^1$ a hydrocarbon group having 1-6, preferably 2-6 carbon atoms)

$$R^2R^3NH \qquad \text{[Formula 34]}$$

(where $R^2$ denotes a hydrocarbon group having 1-12 carbon atoms; and $R^3$ a hydrocarbon group having 1-12 carbon atoms).

A diethylaminotriethoxysilane, or the first or second catalyst component for polymerization or copolymerization catalysts of α-olefins according to the present invention, may be synthesized in the presence of an acid catalyst by reacting a tetrachlorosilane with a tetraethoxysilane at a molar ratio of 1:3 to yield a chlorotriethoxysilane, subsequently reacting a diethylamine with the chlorotriethoxysilane equivalently. At the same time, bis(diethylamino)diethoxysilane, tris (diethylamino)ethoxysilane, and hexaethoxydisiloxane may be produced secondarily.

Third Catalyst Component for Polymerization or Copolymerization Catalysts of α-olefins In the third catalyst component for polymerization or copolymerization catalysts of α-olefins according to the present invention, the reacted mixture component of the trialkoxyhalosilane represented by Formula 35 with the dialkylamine represented by Formula 36 can be employed without isolation and purification. For example, the reacted mixture of XSi(OR$^1$)$_3$ with R$^2$R$^3$NH may be employed in polymerization while it is not filtered and accordingly still contains a secondary product of R$^2$R$^3$NH—HCl. The XSi(OR$^1$)$_3$ and R$^2$R$^3$NH may employ a reacted product added and mixed in the polymerization bath as a (C) component.

In the trialkoxyhalosilane represented by Formula 35, R$^1$ is a hydrocarbon group having 1-6, preferably 2-6 carbon atoms, which may include an unsaturated or saturated aliphatic hydrocarbon group having 1-6 carbon atoms. Specific examples may include methyl group, ethyl group, n-propyl group, isopropyl group, n-butyl group, isobutyl group, t-butyl group, and s-butyl group. The ethyl group is particularly preferable.

In the trialkoxyhalosilane represented by Formula 35, X is halogen, preferably chlor. The trialkoxyhalosilane represented by Formula 35 includes specific examples such as chlortriethoxysilane, chlortrimethoxysilane, and chlortri n-propoxysilane.

In the dialkylamine represented by Formula 36, R$^2$ or R$^3$ is a hydrocarbon group having 1-12 carbon atoms, which may include an unsaturated or saturated aliphatic hydrocarbon group having 1-12 carbon atoms. Specific examples may include methyl group, ethyl group, n-propyl group, isopropyl group, n-butyl group, isobutyl group, t-butyl group, and s-butyl group. The ethyl group is particularly preferable. The dialkylamine represented by Formula 36 may include a diethylamine as a specific example.

Polymerization or Copolymerization Catalysts of α-olefins

The present invention also provides a polymerization or copolymerization catalyst of α-olefins, which contains the first through third catalyst component for polymerization or copolymerization catalysts of α-olefins. The present invention further provides a polymerization or copolymerization catalyst of α-olefins, which comprises [A] a solid catalyst component essentially including magnesium, titanium, a halogen element and an electron donor; [B] an organoaluminum compound component; and [C] the first through third catalyst component for polymerization or copolymerization catalysts of α-olefins.

The present invention employs a solid catalyst component essentially including magnesium, titanium, a halogen element and an electron donor as the component [A]. The process for production of the solid catalyst component of the component [A] is not limited particularly. For example, available processes are proposed in JP-A 54-94590, JP-A 5-55405, JP-A 56-45909, JP-A 56-163102, JP-A 57-63310, JP-A 57-115408, JP-A 58-83006, JP-A 58-83016, JP-A 58-138707, JP-A 59-149905, JP-A 60-23404, JP-A 60-32805, JP-A 61-18330, JP-A 61-55104, JP-A 63-3010, JP-A 1-315406, JP-A 2-77413 and JP-A 2-117905.

Typical processes for production of the solid catalyst component [A] are listed as follows. (1) A process comprises pulverizing a magnesium compound, an electron donor and a titanium halide compound together, or dispersing and solving them in solvent, to bring them in contact with each other for preparation. (2) A process comprises solving a magnesium compound and an electron donor in solvent such as toluene, and adding a titanium halide compound into the solution for reaction to precipitate a catalyst solid.

The magnesium compound available for preparation of the solid catalyst component [A] includes magnesium halide and dialkoxy magnesium. The magnesium halide specifically includes magnesium chloride, magnesium bromide, magnesium iodide, and magnesium fluoride. Particularly, the magnesium chloride is preferable. The dialkoxy magnesium specifically includes dimethoxymagnesium, diethoxymagnesium, din-propoxymagnesium, di n-butoxy magnesium, ethoxymethoxy magnesium, ethoxy n-propoxy magnesium, and buthoxyethoxy magnesium. Particularly, the diethoxy magnesium and the di n-butoxy magnesium are preferable. The dialkoxy magnesium may also be prepared by reacting metal magnesium with alcohol in the presence of halogen or a halogen-containing metal compound. The above dialkoxy magnesium may be employed solely or in combination of two or more.

The dialkoxy magnesium available for preparation of the solid catalyst component [A] may be shaped granular, powdery, indeterminate or spherical. For example, the use of the spherical dialkoxy magnesium leads to production of powders of α-olefin homopolymers or copolymers with other α-olefins which are excellent in morphology and have a narrow particle diameter distribution. The powders are excellent in powder fluidity and accordingly can lead to solution of the problem about clogging hoppers and lines on production.

The titanium halide compound available for preparation of the solid catalyst component [A] includes specific examples of: tetrahalide titanium such as tetrachloro titanium, and tetrabromo titanium; trihalidealkoxy titanium such as trichloromethoxy titanium, trichloroethoxy titanium, trichloropropoxy titanium, trichlorobutoxy titanium, tribromomethoxy titanium, tribromoethoxy titanium, tribromopropoxy titanium, and tribromobuthoxy titanium; dihalidealkoxy titanium such as dichlorodimethoxy titanium, dichlorodiethoxy titanium, dichlorodipropoxy titanium, and dichlorodibutoxy titanium; and halidetrialkoxy titanium such as chlorotrimethoxy titanium, chlorotriethoxy titanium, chlorotripropoxy titanium, and chlorotributoxy titanium. In particular, the tetrachloro titanium is preferable. These titanium halide compounds may be employed solely or in combination of two or more.

The electron donor available for preparation of the solid catalyst component [A] includes a Lewis basic compound, preferably an aromatic diester, preferably a diester orthophthalate. The diester orthophthalate includes specific examples of dimethyl orthophthalate, methylethyl orthophthalate, diethyl orthophthalate, ethyl n-propyl orthophthalate, di n-propyl orthophthalate, n-butyl n-propyl orthophthalate, n-butylethyl orthophthalate, isobutylethyl orthophthalate, di n-butyl orthophthalate, diisobutyl orthophthalate, n-pentyl orthophthalate, diisopentyl orthophthalate, di n-hexyl orthophthalate, b is 2-ethylhexyl orthophthalate, di n-heptyl orthophthalate, and di n-octyl orthophthalate. In particular, the diethyl orthophthalate, the di n-propyl orthophthalate, the di n-butyl orthophthalate, the diisobutyl orthophthalate, the di n-heptyl orthophthalate, the bis 2-ethylhexyl orthophthalate, and the di n-octyl orthophthalate are preferable. These diester orthophthalates may be employed solely or in combination of two or more.

JP-A 3-706, JP-A 3-62805, JP-A 4-270705 and JP-A 6-25332 disclose compounds having two or more ether groups, which may be preferably employed as the electron donor. In addition, WO 00/39171 discloses a diester maleate having a straight or branched chain alkyl group with 2-8 carbon atoms. Among these diester maleates, di n-butyl maleate is particularly preferable.

The organoaluminum compound component [B] of the present invention may include alkyl aluminum or alkyl aluminum halide such as diethyl aluminum chloride, preferably alkyl aluminum, specifically trialkyl aluminum, which include specific examples of trimethyl aluminum, triethyl aluminum, tri-n-propyl aluminum, tri n-butyl aluminum, triisobutyl aluminum, tri-n-hexyl aluminum, and tri n-octyl aluminum. Among those, the triethyl aluminum is particularly preferable. These organoaluminum compound components may be employed solely or in mixture of two or more. Similarly, polyaluminoxan obtained through reaction of alkyl aluminum with water may be employed.

A usage of the organoaluminum compound component [B] as a polymerization catalyst of α-olefins is 0.1-2000, preferably 50-1000 by molar ratio of the solid catalyst component [A] to titanium (Al/Ti).

In the present invention, a mixture of the organosilicon compound represented by the Expression (1) with the organosilicon compound represented by the Expression (2) as the component [C] is added to the above [A] and [B] to form a catalyst system, in which α-olefins can be polymerized or copolymerized. This process is shown in flowchart form in FIG. 1. The component [C] is an organosilicon compound component or a mixture of $Si(OR^1)_3R^2$ with $SiR^3_4$ (where $R^1$ is a hydrocarbon group having 1-4 carbon atoms; $R^2$ is a hydrocarbon group having 1-12 carbon atoms, a primary amino group, or a secondary amino group; $R^3$ is either one of an alkoxy group having 1-4 carbon atoms, a hydrocarbon group having 1-12 carbon atoms, a primary amino group having 1-12 carbon atoms and a secondary amino group having 1-12 carbon atoms. The four $R^3$ on the same molecule may be the same or different from each other. The former and the latter are not the same compound in the above formula.)

A usage of the component [C] is 0.001-10, preferably 0.005-5, and particularly preferably 0.01-1 by molar ratio of the component [B] to aluminum (Si/Al).

The process for polymerization of α-olefins in the present invention may include the following. A slurry polymerization process employs a nonpolar solvent such as propane, n-butane, n-pentane, n-hexane, n-heptane and n-octane. A vapor phase polymerization process brings gaseous monomers into contact with a catalyst for polymerization. A bulk polymerization process employs liquid monomers as a solvent for polymerization therein.

In the above polymerization processes, either continuous polymerization or batch polymerization may be applied, and polymerization reaction may be implemented at a single stage or at multiple stages in combination of the above polymerization processes.

Polymerization of α-olefins

The present invention provides a process for polymerization of α-olefins, which comprises polymerizing or copolymerizing an α-olefin in the presence of the above catalyst.

In the above polymerization process, polymerization pressure is 0.1-20 MPa, preferably 0.5-6 MPa. A polymerization temperature is 10-150° C., preferably 30-100° C., and particularly preferably 60-90° C. A polymerization time is usually 0.1-10 hours, preferably 0.5-7 hours. When the third catalyst component for polymerization or copolymerization catalysts of α-olefins is employed as the catalyst component [C], it is preferable to react and mix the trialkoxyhalosilane represented by Formula 35 with the dialkylamine represented by Formula 36 and then bring the reacted mixture into contact with the organoaluminum compound component [B].

In the present invention, it is preferable to execute preliminary polymerization of ethylene or α-olefin in accordance with the above various polymerization processes, followed by main polymerization of α-olefin. The preliminary polymerization has effects on improvement in polymerization activity, improvement in stereomainity in polymers, and stabilization of morphology in polymers. The solid catalyst component [A] can be brought into contact with the organoaluminum compound component [B] and the component [C] previously to polymerize a limited amount of ethylene or α-olefin for preparation of a preliminarily polymerized solid. Depending on the cases, instead of polymerizing ethylene or α-olefin, a preliminarily processed solid can be prepared by bringing the solid catalyst component [A] into contact with the organoaluminum compound component [B] and the component [C].

In a contact process of the present invention, the component [A], the component [B] and the component [C] are mixed for reaction usually at 0-100° C. for 0.1-100 hours. Though each component may be mixed in order not particularly limited, an order of the component [A], the component [B] and the component [C] is preferable. After the contact process, the solid is cleaned, filtered and separated using an inert hydrocarbon solvent such as n-heptane and employed as the catalyst solid component in the preliminary or main polymerization.

The preliminary polymerization of the present invention can be achieved through a vapor phase polymerization process, a slurry polymerization process or a bulk polymerization process. The solid resulted from the preliminary polymerization may be separated and then employed in main polymerization or continuously subjected to main polymerization without separation.

A preliminary polymerization time is usually 0.1-10 hours and the preliminary polymerization is preferably continued until preliminary polymers are produced in an amount of 0.1-100 g per 1 g of the catalyst solid component. An amount less than 0.1 g per 1 g of the catalyst solid component results in insufficient main polymerization activity, larger catalyst residue, and insufficient stereomainity of α-olefin polymers. An amount more than 100 g may result in lowered polymerization activity and lowered crystallinity of α-olefin polymers. A preliminary polymerization temperature is 0-100° C., preferably 10-70° C. and the preliminary polymerization is performed in the presence of each catalyst component. When preliminary polymerization is performed at a temperature higher than 50° C., it is preferable to reduce the ethylene or α-olefin concentration or shorten the polymerization time. Otherwise, it is difficult to control generation of preliminary polymers in an amount of 0.1-100 g per 1 g of the catalyst solid component. In addition, the polymerization activity may lower in the main polymerization and the crystallinity of resultant α-olefin polymers may lower.

A usage of the organoaluminum compound component [B] on preliminary polymerization is usually 0.5-1000, preferably 1-100 by Al/Ti molar ratio of the solid catalyst component [A] to titanium. A usage of diethylamino triethoxysilane of the component [C] is usually 0.01-5, preferably 0.05-1 by Si/Ti molar ratio to aluminum of the component [B]. On preliminary polymerization, hydrogen may be allowed to coexist, if required.

In the present invention, a chain transfer agent such as hydrogen may be employed. A usage of hydrogen required to produce α-olefin polymers having desired stereomainity, melting point and molecular weight can be determined appropriately based on the polymerization process and condition but usually within a range of hydrogen partial pressure between 0.05-3.

In the present invention, α-olefins may include ethylene, propylene, 1-butene, 1-hexene, and 4-methylpentene-1,3-methylbutene-1,1-octene. In the present invention, for the purposes of lowering the heat seal temperatures of films, lowering the melting points, and improving the transparency of films, they may be copolymerized with other α-olefins.

In addition, to enhance the low-temperature impact strength of moldings originated from α-olefin polymers, a block copolymer may be produced through copolymerization with another two or more α-olefins after homopolymerization of the α-olefins or copolymerization with other α-olefins.

Production of an ethylene-propylene copolymer specifically includes a first step of homopolymerization of propylene or copolymerization of ethylene with propylene, and a subsequent second step of copolymerization of ethylene with propylene. Further, multistage polymerization may be performed in both the first and second steps. The polypropylene resulted from the first step has a melt flow rate ranging between 0.1-2000, preferably 30-1000, and particularly preferably 100-700. The polypropylene resulted from the first step has stereomainity, which is 97.5% or more, preferably 98.0% or more, and particularly preferably 98.2% or more by meso pentad fraction (mmmm). The copolymer of ethylene with propylene produced in the second step has a proportion (block rate=(Yield of the copolymer of ethylene with propylene/Total amount of polymers)×100)) ranging between 1-50 wt. %, preferably 5-35 wt. %.

The catalyst system in the present invention has better hydrogen response, higher polymerization activity, higher stereomainity of resultant α-olefin polymers and better melt fluidity.

The α-olefin polymer resulted from the present invention has higher stereomainity and accordingly is excellent in mechanical physical properties such as stiffness, heat-resistance and tensile strength of injection moldings, which are beneficial in thinning of injection moldings. In addition, it has better melt fluidity and accordingly is possible to shorten the injection molding cycles and resolve appearance failures of moldings such as typical flow marks of injection moldings. Further, the block copolymers with other α-olefins can impart impact resistance. Thus, it is possible to obtain α-olefin polymers excellent in melt fluidity and in balance between stiffness and impact resistance. The α-olefin polymers resulted from the present invention is employed not only solely. It may also employed as a compound material in blend with other plastics and elastomers, and further in mixture with a reinforcement of inorganic or organic filler such as glass fibers and talc or with a crystal nucleus agent. Thus, it is possible to exert excellent performances as structural materials for automobile and household electric appliance though it is not limited.

EXAMPLE 1

Commercially available 0.145 mol of $Si(OEt)_4$ and 0.020 mol of EtOH are supplied into a 100 ml flask with previously nitrogen-replaced internal ambient and agitated at room temperature, followed by dropping 0.050 mol of $SiCl_4$ therein. When EtOH is employed in reaction, it reacts with $SiCl_4$ to generate $Si(OEt)_4$ and HCl in the system formally in accordance with $4EtOH+SiCl_4 \rightarrow Si(OEt)_4+4HCl$. Based on the substance conversion by this expression, a substantial raw material composition is calculated to find that $SiCl_4:Si(OEt)_4=1:3.33$ and that the quantity of the catalyst is 10 mol %. After leaving through the night, the reacted mixture is analyzed in gas chromatography to find generation of $ClSi(OEt)_3$ in an amount of 86% based on prepared Si. Additionally, 80 ml of diethylamine and 500 ml of dehydrated heptane are supplied into a 1000 ml flask with previously nitrogen-replaced internal ambient and, into the solution, the resultant reacted mixture is dropped and agitated for two hours at room temperature. Thereafter, the reacted mixture is analyzed in gas chromatography to find generation of $Et_2NSi(OEt)_3$ in an amount of 75% based on prepared Si.

REFERENTIAL EXAMPLE 1

Commercially available 0.050 mol of $ClSi(OEt)_3$ (96% gas chromatography purity) is reacted with 0.050 mol of diethylamine in the presence of 0.10 mol of triethylamine in 100 ml of heptane at room temperature through the night. As a result, gas chromatography confirms generation of a mixture containing the targeted triethoxy(diethylamino)silane 93% and a tetraethoxysilane 6%.

From the results of Example 1 and Referential Example 1, it can be determined that the amination reaction at the second step in the continuous reactions proceeds by about 93±3% in consideration of accuracy of the gas chromatography analysis. It is obvious that the yield at the first step in the continuous reactions is substantially a large factor that varies the yield as a whole. Therefore, in the following Examples 2-8, the first step in the continuous reactions, that is, production of trialkoxyhalosilanes, is described.

EXAMPLE 2

Commercially available 0.150 mol of $Si(OEt)_4$ and 0.020 mol of EtOH are supplied into a 100 ml flask with previously nitrogen-replaced internal ambient and agitated at room temperature, dropping 0.050 mol of $SiCl_4$ therein. A substantial raw material composition is $SiCl_4:Si(OEt)_4=1:3.44$ and the quantity of the catalyst is 10 mol %. After leaving through the night, the reacted mixture is analyzed in gas chromatography to find generation of 82% $ClSi(OEt)_3$ and residue of 11% $Si(OEt)_4$ based on prepared Si.

EXAMPLE 3

The reaction is similarly performed as in Example 2 except that 0.170 mol of $Si(OEt)_4$ is employed instead of 0.150 mol of $Si(OEt)_4$. A substantial raw material composition is $SiCl_4:Si(OEt)_4=1:3.89$ and the quantity of the catalyst is 9 mol %. The product is analyzed to find generation of 77% $ClSi(OEt)_3$ and residue of 19% $Si(OEt)_4$ based on prepared Si.

EXAMPLE 4

The reaction is similarly performed as in Example 2 except that 0.155 mol of $Si(OEt)_4$ is employed instead of 0.150 mol of $Si(OEt)_4$. A substantial raw material composition is $SiCl_4:Si(OEt)_4=1:3.56$ and the quantity of the catalyst is 10 mol %. The product is analyzed to find generation of 79% $ClSi(OEt)_3$ and residue of 12% $Si(OEt)_4$ based on prepared Si.

EXAMPLE 5

The reaction is similarly performed as in Example 2 except that 0.140 mol of $Si(OEt)_4$ is employed instead of 0.150 mol of $Si(OEt)_4$. A substantial raw material composition is $SiCl_4$:

Si(OEt)$_4$=1:3.22 and the quantity of the catalyst is 11 mol %. The product is analyzed to find generation of 81% ClSi(OEt)$_3$ and residue of 13% Si(OEt)$_4$ based on prepared Si.

EXAMPLE 6

The reaction is similarly performed as in Example 2 except that 0.135 mol of Si(OEt)$_4$ is employed instead of 0.150 mol of Si(OEt)$_4$. A substantial raw material composition is SiCl$_4$:Si(OEt)$_4$=1:3.11 and the quantity of the catalyst is 11 mol %. The product is analyzed to find generation of 85% ClSi(OEt)$_3$ and residue of 10% Si(OEt)$_4$ based on prepared Si.

EXAMPLE 7

The reaction is similarly performed as in Example 2 except that 0.130 mol of Si(OEt)$_4$ is employed instead of 0.150 mol of Si(OEt)$_4$. A substantial raw material composition is SiCl$_4$:Si(OEt)$_4$=1:3.00 and the quantity of the catalyst is 11 mol %. The product is analyzed to find generation of 84% ClSi(OEt)$_3$ and residue of 11% Si(OEt)$_4$ based on prepared Si.

EXAMPLE 8

The reaction is similarly performed as in Example 2 except that 0.115 mol of Si(OEt)$_4$ is employed instead of 0.150 mol of Si(OEt)$_4$. A substantial raw material composition is SiCl$_4$:Si(OEt)$_4$=1:2.67 and the quantity of the catalyst is 12 mol %. The product is analyzed to find, generation of 75% ClSi(OEt)$_3$ and residue of 7% Si(OEt)$_4$ based on prepared Si.

COMPARATIVE EXAMPLE 1

Commercially available 0.167 mol of Si(OEt)$_4$ and 0.020 mol of trifluoro acetate are supplied into a 100 ml flask with previously nitrogen-replaced internal ambient and agitated at room temperature, dropping 0.050 mol of SiCl$_4$ therein. A raw material composition is SiCl$_4$:Si(OEt)$_4$=1:3.33 and the quantity of the catalyst is 9 mol %. After leaving through the night, the reacted mixture is analyzed in gas chromatography to find generation of 73% ClSi(OEt)$_3$ and residue of 16% Si(OEt)$_4$ based on prepared Si.

COMPARATIVE EXAMPLE 2

The reaction is similarly performed as in Comparative Example 1 except that 0.020 mol of acetic acid is employed instead of 0.020 mol of trifluoro acetate. After leaving through the night, the reacted mixture is analyzed in gas chromatography to find generation of 61% ClSi(OEt)$_3$ and residue of 20% Si(OEt)$_4$ based on prepared Si.

COMPARATIVE EXAMPLE 3

The reaction is similarly performed as in Comparative Example 1 except that sulfuric acid carrier silica (0.010 mol as an amount of sulfuric acid) is employed instead of 0.020 mol of trifluoro acetate. After leaving through the night, the reacted mixture is analyzed in gas chromatography to find generation of 27% ClSi(OEt)$_3$ and residue of 18% Si(OEt)$_4$ based on prepared Si.

EXAMPLE 9

In a 500 ml four-neck flask equipped with a nitrogen introduction tube, a thermometer and a dropping funnel, 139.9 g (0.669 mol) of tetraethoxysilane and 9.2 g (21 mol % based on a total amount of Si) (0.20 mol) are prepared and water-cooled, dropping 46.5 g (0.274 mol) of tetrachlorosilane therein for 10 minutes in nitrogen ambient. After completion of dropping, through agitation at 25° C. for 2 hours, the reacted solution is analyzed in gas chromatography to find generation of 0.839 mol of chlorotriethoxysilane. Expression 2 is employed to find a yield of 89.0% based on prepared Si.

Si-based yield(mol %)=Produced chlorotriethoxysilane(mol)/(Prepared tetraethoxysilane(mol)+Prepared tetrachlorosilane(mol))    [Expression 2]

In a 3 L four-neck flask equipped with an agitator, a nitrogen introduction tube, a thermometer and a dropping funnel, 570 g (7.79 mol) of diethylamine is prepared and water-cooled, agitating and dropping the reacted mixture in nitrogen ambient for 30 minutes. The internal temperature is kept at 25-30° C. during this process. After completion of dropping, through agitation for 2 hours, 1 L of n-heptane is added, followed by further agitation for 10 minutes. The reacted solution is filtered under pressure, then condensed under reduced pressure, and distilled under reduced pressure of 4 Torr at 62-63° C. in an Oldershow distillation column with 10 logical stages. As a result, 144.3 g (0.613 mol) of diethylaminotriethoxysilane is obtained. Expression 3 is employed to find a yield of 65.0% based on prepared Si.

Si-based yield(mol %)=Obtained diethylaminotriethoxysilane(mol)/(Prepared tetraethoxysilane(mol)+Prepared tetrachlorosilane(mol))    [Expression 3]

COMPARATIVE EXAMPLE 4

The reaction and operation are similarly performed as in Example 9 except that 2.4 g of ethanol (5.5 mol % based on a total amount of Si) (0.052 mol) is employed. As a result, a yield of chlorotriethoxysilane in the reaction at the first step is 14.4% based on prepared Si, and an obtained yield of diethylaminotriethoxysilane through distillation after the reaction at the second step is 8.6% based on prepared Si.

COMPARATIVE EXAMPLE 5

The reaction and operation are similarly performed as in Comparative Example 4 except that the reaction time is changed to 24 hrs. As a result, a yield of chlorotriethoxysilane in the reaction at the first step is 72.3% based on prepared Si, and an obtained yield of diethylaminotriethoxysilane through distillation after the reaction at the second step is 52.2% based on prepared Si.

EXAMPLE 10

The reaction and operation are similarly performed as in Example 9 except that 7.0 g of ethanol (16 mol % based on a total amount of Si) (0.15 mol) is employed. As a result, a yield of chlorotriethoxysilane in the reaction at the first step is 87.5% based on prepared Si, and an obtained yield of diethylaminotriethoxysilane through distillation after the reaction at the second step is 63.9% based on prepared Si.

EXAMPLE 11

The reaction and operation are similarly performed as in Example 9 except that 4.6 g of ethanol (11 mol % based on a total amount of Si) (0.10 mol) is employed and the reaction temperature at the first step is changed to 40° C. As a result, a yield of chlorotriethoxysilane in the reaction at the first step is 78.2% based on prepared Si, and an obtained yield of diethylaminotriethoxysilane through distillation after the reaction at the second step is 57.3% based on prepared Si.

EXAMPLE 12

Commercially available 0.145 mol of $SiCl_4$ is supplied in a 100 ml four-neck flask with previously nitrogen-replaced internal ambient, and cooled down to about 2° C. in ice bath. It is then agitated well while a micro feeder is employed for one hour to inject 0.440 mol of EtOH into $SiCl_4$. In this case, a molar ratio of $EtOH/SiCl_4$ is 3.0. During injection, the reaction temperature gradually lowers and finally reaches to −20° C. Then, through agitation for 3 hours, the reacted mixture is analyzed in gas chromatography to find generation of 87% $ClSi(OEt)_3$ based on prepared Si. Additionally, 125 ml of diethylamine is supplied into a 1000 ml flask with previously nitrogen-replaced internal ambient and, into the solution, the reacted mixture is dropped and agitated for 3 hours at room temperature. Thereafter, the reacted mixture is analyzed in gas chromatography to find generation of $Et_2NSi(OEt)_3$ in an amount of 79% based on prepared Si.

From the results of Example 12 and Referential Example of Example 1, it is obvious like Example 1 that the yield at the first step in the continuous reactions is substantially a large factor that varies the yield as a whole. Therefore, in the following Referential Examples, the first step in the continuous reactions, that is, production of trialkoxyhalo silanes, is described.

EXAMPLE 13

With a molar ratio $EtOH/SiCl_4$ of 3.4, the reaction of $SiCl_4$ with EtOH is performed under the same operation as in Example 12. Then, the reacted mixture is analyzed in gas chromatography to find generation of $ClSi(OEt)_3$ in an amount of 57%.

EXAMPLE 14

With a molar ratio $EtOH/SiCl_4$ of 3.3, the reaction of $SiCl_4$ with EtOH is performed under the same operation as in Example 12. Then, the reacted mixture is analyzed in gas chromatography to find generation of $ClSi(OEt)_3$ in an amount of 67%.

EXAMPLE 15

With a molar ratio $EtOH/SiCl_4$ of 3.2, the reaction of $SiCl_4$ with EtOH is performed under the same operation as in Example 12. Then, the reacted mixture is analyzed in gas chromatography to find generation of $ClSi(OEt)_3$ in an amount of 77%.

EXAMPLE 16

With a molar ratio $EtOH/SiCl_4$ of 3.1, the reaction of $SiCl_4$ with EtOH is performed under the same operation as in Example 12. Then, the reacted mixture is analyzed in gas chromatography to find generation of $ClSi(OEt)_3$ in an amount of 86%.

EXAMPLE 17

With a molar ratio $EtOH/SiCl_4$ of 3.05, the reaction of $SiCl_4$ with EtOH is performed under the same operation as in Example 12. Then, the reacted mixture is analyzed in gas chromatography to find generation of $ClSi(OEt)_3$ in an amount of 87%.

EXAMPLE 18

With a molar ratio $EtOH/SiCl_4$ of 2.95, the reaction of $SiCl_4$ with EtOH is performed under the same operation as in Example 12. Then, the reacted mixture is analyzed in gas chromatography to find generation of $ClSi(OEt)_3$ in an amount of 87%.

EXAMPLE 19

With a molar ratio $EtOH/SiCl_4$ of 2.9, the reaction of $SiCl_4$ with EtOH is performed under the same operation as in Example 12. Then, the reacted mixture is analyzed in gas chromatography to find, generation of $ClSi(OEt)_3$ in an amount of 90%.

EXAMPLE 20

With a molar ratio $EtOH/SiCl_4$ of 2.0, the reaction of $SiCl_4$ with EtOH is performed under the same operation as in Example 12. Then, the reacted mixture is analyzed in gas chromatography to find generation of $ClSi(OEt)_3$ in an amount of 88%.

EXAMPLE 21

Examples of the polymerization or copolymerization catalysts of α-olefins according to the present invention will be described below though the present invention is not limited at all by the description of the following Examples. In Examples 21-26, the polymerization activity represents a yield (g) of α-olefin polymers obtained in one hour of polymerization per 1 g of the solid catalyst. H. I. indicates a proportion (Weight of insoluble polymers/Weight of prepared polymers×100) when α-olefin polymers are subjected to an extraction test in boiled n-heptane for 6 hours. A melt flow rate (MFR) is measured based on ASTM-D1238. It indicates the weight (g) of a melt polymer at 230° C. under load of 2.16 Kg for 10 minutes. The melt flow rate is employed as an index of hydrogen response. Namely, under condition of α-olefin polymerization at the same hydrogen concentration, the higher the numeral value the higher the hydrogen response becomes, and the lower the numeral value the lower the hydrogen response becomes. The meso pentad fraction (mmmm) % obtained through examination of micro-tacticity or the index of stereomainity of α-olefin polymers is calculated from a peak strength ratio in 13C-NMR spectrum belonging in propylene polymers based on Macromolecules 8, 687 (1975). The $^{13}$C-NMR spectrum is measured using a device EX-400 available from Nippon Electronics with reference to TMS at a temperature of 130° C. in an o-dichlorobenzen solvent, scanning 8000 times.

The component [C] of the organosilicon compound is synthesized as shown below. First, into a four-neck flask having a 1 L volume and equipped with a sufficiently nitrogen-replaced magnet seal agitator and a dropping funnel, 0.14 mol of tetrachlorosilane, 0.34 mol of tetraethoxysilane and 0.022 mol of trifluoro acetate are introduced in turn. Then, they are subjected to reaction at room temperature for 3 hours, and further subjected to reaction at 60° C. for 7 hours. Subsequently, 1.92 mol of diethylamine previously introduced into the dropping funnel is dropped. After completion of dropping, they are subjected to reaction at room temperature for 9 hours. After completion of the reaction, the reacted solution is collected partly to confirm generation of the target product in gas chromatography. Thereafter, in nitrogen ambient, the reacted solution in the flask is entirely transferred into a container equipped with a G3 glass filter and subjected to pressurized filtration with low-pressure nitrogen of 0.01 MPa. Further, a hydrochloride of diethylamine of filtrated residue is cleaned and filtrated repeatedly with n-heptane until the target product can not be confirmed in the filtrated solution. The cleaned mixture of the filtrated solution and the filtrated residue is condensed under reduced pressure to remove the solvent components such as n-heptane through distillation and collect the target product. The target product has an appearance of colorless transparent liquid and a boiling point of 58.0° C./mHg.

The purity of the component [C] is represented by wt. % derived from a peak area ratio in gas chromatography using a calibration curve. A gas chromatography device of GC-14A (available from Shimazu) is employed and a hydrogen flame ion detector is employed. A column of G-100, 20 m, 1.2 mm inner diameter, 2 μm film thickness (available from GL Science) is employed. An injection temperature and a detector temperature are at 280° C. Under a temperature elevating condition, an initial column temperature is kept at 70° C. for 10 minutes, then the temperature is elevated up to 260° C. at a rate of 16° C./min, and finally kept at 260° C. for 10 minutes.

As a result of the gas chromatography analysis under the above condition, the product has a composition of diethylamino triethoxysilane 91.5 wt. %, diethylamine 0.1 wt. %, tetraethoxy silane 1.6 wt. %, diethylaminodiethoxymethoxysilane 1.1 wt. %, bis(diethylamino)diethoxysilane 5.2 wt. %, and hexaethoxy disiloxane 0.5 wt. %. The products are identified in gas chromatography and mass spectra thereof are shown in FIGS. 2-7.

As the solid catalyst component [A] for use in polymerization of propylene, a THC-TC type commercially available from Toho Catalyst is employed. The Ti content is 1.7 wt. %.

Propylene is polymerized using an agitator-equipped autoclave of stainless steel with a 2 L inner volume. First, the interior of the autoclave is sufficiently replaced with nitrogen. Then, 0.0025 mmol on titanium atom basis of n-heptane slurry of the solid catalyst component [A], 2 mmol of triethyl aluminum as the organoaluminum compound component [B], and 0.36 mmol of previously obtained purity 91.5 wt. % diethyl aminotriethoxysilane as the organosilicon compound component [C] are supplied in the autoclave. Subsequently, 0.4 MPa hydrogen and 1.2 L liquidized propylene are introduced in turn. The interior of the autoclave is cooled down to 10° C., followed by preliminary polymerization for 10 minutes. Subsequently, the temperature inside the autoclave is elevated up to 70° C., followed by further polymerization at 70° C. for one hour under polymerization pressure of 3.8 MPa. After completion of the polymerization, non-reacted propylene gas is discharged and the polymer is dried at 60° C. for 20 hours to produce white powdery polypropylene. The results are shown in Table 1.

EXAMPLE 22

The organosilicon compound component [C] is synthesized as shown below. First, into a sufficiently nitrogen-replaced 100 ml volume three-neck flask equipped with a dropping funnel, 30 ml of diethylamine is introduced, and 0.015 mol of dichloro diethoxysilane previously introduced into the dropping funnel is dropped therein at room temperature. After completion of dropping, 30 ml of diethylamine is added and they are subjected to reaction at room temperature for 4 hours.

After completion of the reaction, the reacted solution is collected partly to confirm generation of the target product in gas chromatography. Thereafter, in nitrogen ambient, the reacted solution in the flask is entirely transferred into a container equipped with a G3 glass filter and subjected to pressurized filtration with low-pressure nitrogen of 0.01 MPa. Further, a hydrochloride of diethylamine of filtrated residue is cleaned and filtrated repeatedly with diethylamine until the target product can not be confirmed in the filtrated solution. The cleaned mixture of the filtrated solution and the filtrated residue is condensed under reduced pressure to remove the solvent components and collect the target product through distillation and purification. The target product has an appearance of colorless transparent liquid and a boiling point of 109° C./9 mmHg. As a result of the gas chromatography analysis, the product has a composition of bis(diethylamino) diethoxysilane 97.7 wt. %, diethylamine 0.7 wt. %, diethylaminodiethoxymethoxysilane 0.2 wt. %, diethylaminotriethoxysilane 0.8 wt. %, and hexaethoxy disiloxane 0.6 wt. %.

The above resultant bis(diethylamino)diethoxysilane 97.7 wt. % is mixed with the diethylaminotriethoxysilane 91.5 wt. % resulted from Example 21 at a weight ratio of 1:1. Polymerization of propylene is performed as in Example 1 except that this mixture is employed as the component [C]. The results are shown in Table 1.

COMPARATIVE EXAMPLE 6

Polymerization of propylene is performed as in Example 21 except that cyclohexylmethyldimethoxysilane is employed as the organosilicon compound component [C]. The results are shown in Table 1.

TABLE 1

| | POLYMERIZATION ACTIVITY g-PP/g-Cat. hr | MFR g/10 min | H.I % | mmmm % |
|---|---|---|---|---|
| EXAMPLE 21 | 41,400 | 400 | 96.8 | 98.8 |
| EXAMPLE 22 | 41,500 | 533 | 95.6 | 98.6 |
| COMPARATIVE EXAMPLE 6 | 42,600 | 76.5 | 97 | 98.2 |

EXAMPLE 23

Polymerization of propylene is implemented as follows. First, a 2 L inner volume stainless steel autoclave equipped with a magnet seal agitator is sufficiently nitrogen-replaced in the interior thereof. Into the autoclave, 2.2 mmol of triethyl aluminum as the organoaluminum compound component [B], 0.36 mmol of dietylaminotirethoxysilane resulted from the present invention as the component [C], and $2.5 \times 10^{-3}$ mmol of n-heptane slurry on titanium atom basis as the solid catalyst component [A] of the THC-JC type available from Toho Catalyst are introduced in turn. Then, hydrogen (0.4 MPa) and liquidized propylene (1.2 L) are introduced. Subsequently, the temperature inside the autoclave is elevated up to 70° C., followed by polymerization at 70° C. for one hour under polymerization pressure of 3.8 MPa. After completion of the polymerization, non-reacted propylene gas is discharged and the polymer is dried at 60° C. for 20 hours to produce white powdery polypropylene. The polymerization activity is 42 kg/g-Cat. hr, MFR is 400 g/10 min, H.I is 96.2%, and mmmm is 98.8%.

EXAMPLE 24

The solid catalyst component [A] for use in polymerization of propylene is the THC-JC type available from Toho Catalyst. The content of Ti is 1.7 wt. %.

Propylene is polymerized using an agitator-equipped autoclave of stainless steel with a 2 L inner volume. First, the interior of the autoclave is sufficiently replaced with nitrogen. Then, 0.0025 mmol on titanium atom basis of n-heptane slurry of the solid catalyst component [A], 0.36 mmol of chlortriethoxysilane and 0.72 mmol of diethylamine as the (C) component, and 2 mmol of triethyl aluminum as the (B) component are supplied in the autoclave. Subsequently, 0.4 MPa hydrogen and 1.2 L liquidized propylene are introduced in turn. The interior of the autoclave is cooled down to 10° C., followed by preliminary polymerization for 10 minutes. Subsequently, the temperature inside the autoclave is elevated up to 70° C., followed by further polymerization at 70° C. for one hour under polymerization pressure of 3.8 MPa. After completion of the polymerization, non-reacted propylene gas is discharged and the polymer is dried at 60° C. for 20 hours to produce white powdery polypropylene. The polymerization activity is 35,800 g-PP/g-Ct. hr, MFR is 615, H.I is 95.9, and the meso pentad fraction (mmmm) is 97.9.

EXAMPLE 25

As the component (C), the reacted mixture additionally mixed with chlortriethoxysilane and diethylamine and filtrated is employed while others are similar to those in Example 1. The polymerization activity is 41,800 g-PP/g-Ct. hr, MFR is 400, H.I is 96.6, and the meso pentad fraction (mmmm) is 98.5.

EXAMPLE 26

As the component (C), the reacted mixture additionally mixed with 0.36 mmol of chlortriethoxysilane and 0.72 mmol of diethylamine and filtrated is employed while others are similar to those in Example 2. The polymerization activity is 43,400 g-PP/g-Ct. hr, MFR is 444, H.I is 96.2, and the meso pentad fraction (mmmm) is 98.4.

EXAMPLE 27

As the component (B), only chlortriethoxysilane is employed and diethylamine is not employed while others are similar to those in Example 1. The polymerization activity is 32,900 g-PP/g-Ct. hr, MFR is 799, H.I is 94.9, and the meso pentad fraction (mmmm) is 97.5.

The invention that is claimed is:

1. A process for production of trialkoxy(dialkylamino) silanes, comprising:
a first step which comprises reacting a tetrahalosilane represented by Formula 1 with a tetraalkoxysilane represented by Formula 2 in the mixture of an alcohol composed of the same alkoxy group as that of the tetraalkoxysilane to yield a trialkoxyhalosilane represented by Formula 3, wherein the alcohol is used in an amount of 10-50% by mol based on a total amount of Si in the tetrahalosilane and the tetraalkoxysilane:

$$SiX_4 \quad \text{[Formula 1]}$$

(where X denotes halogen)

$$Si(OR^1)_4 \quad \text{[Formula 2]}$$

(where $R^1$ denotes a hydrocarbon group having 1-6 carbon atoms)

$$XSi(OR^1)_3 \quad \text{[Formula 3]}$$

(where X denotes halogen; and $R^1$ a hydrocarbon group having 1-6 carbon atoms); and
and a second step of reacting the trialkoxy halosilane obtained in the first step with a dialkylamine represented by Formula 7 to yield a trialkoxy(dialkylamino) silane represented by Formula 8:

$$R^2R^3NH \quad \text{[Formula 7]}$$

(where $R^2$ denotes a hydrocarbon group having 1-12 carbon atoms; and $R^3$ a hydrocarbon group having 1-12 carbon atoms)

$$R^2R^3NSi(OR^1)_3 \quad \text{[Formula 8]}$$

(where $R^1$ denotes a hydrocarbon group having 1-6 carbon atoms; $R^2$ a hydrocarbon group having 1-12 carbon atoms; and $R^3$ a hydrocarbon group having 1-12 carbon atoms).

2. The process for production of trialkoxy(dialkylamino) silanes according to claim 1, wherein the reacted mixture obtained in the first step is reacted with the dialkylamine represented by Formula 7, without subjecting to isolation/purification.

3. The process for production of trialkoxy(dialkylamino) silanes according to claim 1, wherein X is chlorine and $R^1$, $R^2$ and $R^3$ are ethyl in the compound represented by Formulae 1-3, 7, and 8.

4. The process for production of trialkoxy(dialkylamino) silanes according to claim 2, wherein X is chlorine and $R^1$, $R^2$ and $R^3$ are ethyl in the compound represented by Formulae 1-3, 7, and 8.

* * * * *